US005764352A

United States Patent [19]

Kappel et al.

[11] Patent Number: 5,764,352

[45] Date of Patent: Jun. 9, 1998

[54] PROCESS AND APPARATUS FOR SPECTRAL REFLECTANCE AND TRANSMISSION MEASUREMENTS

[75] Inventors: Peter Kappel, Limeshain; Werner Lenz, Langenselbold; Walter Müller, Steinau/Umbach; Christian Schäffer, Gelnhausen; Wilhelm Schebesta, Jena; Ulrich Basler, Jena; Jens Mondry, Jena; Jürgen Gobel, Jena, all of Germany

[73] Assignee: Balzers UND Leybold Deutschland Holding AG, Hanau, Germany

[21] Appl. No.: 691,137

[22] Filed: Aug. 1, 1996

[30] Foreign Application Priority Data

Aug. 5, 1995 [DE] Germany ........................ 195 28 855.6

[51] Int. Cl.$^6$ ........................ G01J 1/42

[52] U.S. Cl. ........................ 356/225; 356/213; 356/222; 356/73

[58] Field of Search ........................ 356/225, 213, 356/222, 73

[56] References Cited

U.S. PATENT DOCUMENTS

| | | | |
|---|---|---|---|
| 3,874,799 | 4/1975 | Isaacs | 356/173 |
| 4,093,991 | 6/1978 | Christie, Jr. et al. | 364/525 |
| 4,565,444 | 1/1986 | Mactaggart | 356/73 |
| 4,669,873 | 6/1987 | Wirz | 356/73 |
| 4,770,530 | 9/1988 | Van Aken et al. | 356/323 |
| 4,802,763 | 2/1989 | Gerlinger et al. | 356/319 |
| 4,878,757 | 11/1989 | Westphal | 356/225 |
| 4,919,535 | 4/1990 | Hohberg et al. | 356/429 |
| 4,948,256 | 8/1990 | Lin et al. | 358/328 |
| 4,961,646 | 10/1990 | Schrammli et al. | 356/328 |
| 5,384,641 | 1/1995 | Imura | 356/446 |
| 5,453,829 | 9/1995 | Remer et al. | 356/225 |
| 5,481,380 | 1/1996 | Bestmann | 358/504 |
| 5,497,229 | 3/1996 | Sensui et al. | 356/225 |

FOREIGN PATENT DOCUMENTS

| | | |
|---|---|---|
| 8121760 | of 1983 | France . |
| 2606675 | of 1977 | Germany . |
| 3103971 | of 1982 | Germany . |
| 9005845.3 | of 1990 | Germany . |
| 4120749 | of 1992 | Germany . |

OTHER PUBLICATIONS

Abele, "Industrieroboter in der Montage" Technische Rundschau 26/85, S. 26, 28–31, 33.

*Primary Examiner*—David C. Nelms
*Assistant Examiner*—Reginald A. Ratliff
*Attorney, Agent, or Firm*—Felfe & Lynch

[57] ABSTRACT

Optical measuring apparatus for determining chromaticity of thin films on a substrate includes a light source for illuminating the substrate and a measuring apparatus for dispersing light into various wavelengths and making wavelength dependent intensity measurements. Radiation from the light source is reflected or transmitted by the substrate to the measuring apparatus along a first beam path having a first diaphragm for cutting off the radiation from the substrate in a leak-tight manner. Radiation from the light source is also transmitted to the measuring apparatus directly along a second beam path having a second diaphragm for cutting off radiation from the light source in a leak-tight manner. The light source (6a) consists of a globe photometer (6a), in which a lamp (4) is provided. A steadily burning light source, especially a halogen lamp, is used as the lamp (4). Long-term instabilities are corrected essentially by means of a white reference standard, whereas short-term instabilities are corrected under consideration of the characteristic emission spectrum of the selected lamp (4). For determining the chromaticity of reflecting and transparent thin-film layers applied to substrate, a process for reflectance curve determination is used, in which apparatus-related instabilities interfering with the chromaticity measurement are corrected by normalization of the measured relative spectral energy distributions to the current measurement light spectrum and by taking into consideration the effects of foreign light on the measurement light spectrum.

17 Claims, 2 Drawing Sheets

COMPUTER

COMPUTER
17
15
29
31
14
16
10a
10b
11a
11b
8a
8b
13
6b
4
22b
2b
3b
27
24
20
9
A
C
1

COMPUTER
17
15
29
31
14
16
10b
10a
11b
11a
8b
8a
13
4
22a
2a
3a
20
9
27
24
A
1
6a
26
B
5

PROCESS AND APPARATUS FOR SPECTRAL REFLECTANCE AND TRANSMISSION MEASUREMENTS

BACKGROUND OF THE INVENTION

The invention pertains to a process for measuring the optical properties of transparent and/or reflecting objects and also to an optical measuring apparatus for implementing the process.

In the production and/or quality control of optical products, it is frequently necessary to measure and graphically display certain optical properties such as the reflection and transmission behavior as a function of the wavelength of the light or to process the optical measurement variables in additional computational and evaluation procedures. An example of this is the optical analysis of the filter layers provided as infrared filters, which are intended to block thermal radiation but allow visible light to pass through with a minimum of hindrance. Filter layers of this type are used most often as coatings on architectural glass and coatings on the windows of motor vehicles. Another example is antireflective coatings, especially for wideband antireflection treatments, which are intended to reduce the reflections within the range of visible light to the maximum possible extent. It is necessary to measure the behavior of these layers as a function of wavelength both during the production of the layers and during the final inspection of the optical layer.

The conventional method for characterizing the spectral reflectivity or transmission ability of optical coatings, especially those produced by a thin-layer process, is to detect the reflection and/or transmission spectrum in terms of intensity over the wavelength range of interest to obtain a so-called relative spectral energy distribution. On the basis of these relative spectral energy distributions, it is possible to determine the chromaticity of the coated substrates, which is characteristic of the optical properties of the substrates themselves. A general problem which occurs in measurements of this type is that of determining the relative spectral energy distributions in a way which is independent of the wavelength-dependent optical transmission properties of the detection channels. In addition, temporal instabilities in the emission characteristics of the light sources caused by long-term effects such as aging, or interfering short-term effects such as fluctuations in the supply voltage, or in the ambient temperature, make it impossible to analyze the chromaticity in a reproducible and reliable manner. These relative spectral energy distribution measurements are also affected by instabilities in the optical detection channels of the selected light-dispersing devices such as spectrometers and in the photodetecting devices such as photomultipliers or CCD (charge coupled device) detectors used to detect the light. In addition, it is necessary to record the relative spectral energy distributions of the test piece surfaces without any interfering effects being exerted on them by the prevailing characteristic emission spectrum of the light source used to illuminate the measurement field or by the spectral sensitivity curve of the detectors being used. Otherwise the relative spectral energy distributions of the same test piece surface measured with two different light sources, for example, cannot be compared with each other and thus lose their information value for the observer. It is a disadvantage that reproducible values cannot be obtained.

SUMMARY OF THE INVENTION

The object of the invention is to provide a measurement method and a measuring device for determining chromaticity from relative spectral energy distributions measured on a reflecting and/or transparent test piece, in which the time-variant measurement artifacts attributable to both long-term and short-term instabilities are eliminated.

The chromaticity is determined essentially in two steps. First, the diffuse reflectance curve $\beta(\lambda)$ is measured by means of spectrophotometry, then the diffuse reflectance curve $\beta(\lambda)$ is evaluated mathematically to determine the chromaticity. To measure the diffuse reflectance curve $\beta(\lambda)$, a portion of the test piece surface is illuminated locally by a light source, and the light reflected by the test piece surface is broken down into its spectrum by a light-dispersing device and measured in terms of its intensity by a photodetector device. The diffuse reflectance curve $\beta(\lambda)$ is thus:

$$\beta(\lambda)=\frac{\beta_P(\lambda)-\beta_S(\lambda)}{\beta_R(\lambda)-\beta_S(\lambda)}. \tag{I}$$

where:

$$\beta_P(\lambda)=\frac{\Phi_P(\lambda)}{\Phi_{k1}(\lambda)}, \tag{II}$$

$$\beta_R(\lambda)=\frac{\Phi_R(\lambda)}{\Phi_{k2}(\lambda)}, \tag{III}$$

$$\beta_S(\lambda)=\frac{\Phi_S(\lambda)}{\Phi_{k3}(\lambda)} \tag{IV}$$

where:

$\Phi_P(\lambda)$=the relative spectral energy distribution measured on the test piece;

$\Phi_R(\lambda)$=the relative spectral energy distribution measured on a reference surface; and $\Phi_S(\lambda)$=the relative spectral energy distribution of the test piece background.

The relative spectral energy distributions $\Phi_{Ki,i=1-3}(\lambda)$ define the characteristic spectrum of the light produced by the lamp. For reflected light measurements according to the invention, the relative spectral energy distributions $\Phi_P(\lambda)$, $\Phi_R(\lambda)$, and $\Phi_S(\lambda)$ are measured individually first, and then the characteristic emission spectrum of the illumination source, which undergoes short-term fluctuations, is determined by measurement of $\Phi_{ki,i=1-3}(\lambda)$ immediately after the associated relative spectral energy distributions are found. By measuring the individual relative spectral energy distributions $\Phi_{ki,i=1-3}(\lambda)$ immediately after the measurement of $\Phi_P$, $\Phi_R$, and $\Phi_S$, it is advantageously ensured that, when the function ratios are calculated, $\beta_P$, $\beta_R$, $\beta_S$ in Equations II, III, and IV are normalized to the current spectrum of the lamp.

For transmitted light measurements, the relative spectral energy distributions $\Phi_P(\lambda)$ and $\Phi_R(\lambda)$ are measured along with the associated $\Phi_{ki,i=1,2,3}(\lambda)$. To calculate $\beta(\lambda)$ in Equation (I), $\beta_S(\lambda)$ is set as a constant with a value of zero. The effects of short-term fluctuations in the intensity curve of the lamp spectrum on $\beta_P(\lambda)$, $\beta_R(\lambda)$, and $\beta_S(\lambda)$ are therefore excluded, which is advantageous. If the intensity of the light source proves to be unstable within a measurement cycle, each of the individual the relative spectral energy distributions $\Phi(\lambda)$ is preferably measured several times and the average values are calculated by adding up the values obtained for the individual relative spectral energy distributions over the course of several individual measurement cycles.

Preferably, only a single detection channel, in particular only a single light-dispersing, spectrum-resolving device, and one light-sensitive photodetector are used. As a result, any differences which might exist with respect to the response behavior of the individual detection channels of different detection devices used separately to measure $\Phi_{R,S,P}(\lambda)$ and $\Phi_{ki,i=1,2,3}$ are eliminated.

To take into account the long-term instabilities of the measuring devices used, $\beta_P(\lambda)$ is normalized to the reflection spectrum of a white reference standard. The white reference standard used here is the surface of a press-molded piece of barium sulfate or a flat body, preferably made of magnesium oxide or ceramic material.

If, for the lower definition point of the $\beta_P(\lambda)$ or $\beta_R(\lambda)$ scale, it is not true that $\beta(\lambda)=0$, which corresponds to the emission characteristic of a blackbody, but rather that $\beta_S(\lambda) \neq 0$ and/or that, during the measurement of $\Phi_P(\lambda)$ and $\Phi_R(\lambda)$, the influence of foreign light sources plays a role, it is necessary to make an additional dark compensation measurement to determine $\beta_S(\lambda)$, as included in Equation (I) above.

A globe photometer (Ulbricht sphere) is preferably used as the illumination source, the interior of which is lighted by a light source. A halogen lamp or the exit end of a fiber-optics waveguide projecting into the globe photometer is provided as the light source. This has the advantage that the thermal load on the globe photometer caused by a heat-emitting light source is avoided, and thus thermal effects which could negatively influence the emission spectrum of the light source cannot occur.

The globe photometer used as the light source for the detection of the relative spectral energy distributions $\Phi_{ki,i=1,2,3}(\lambda)$ has a second light outlet essentially perpendicular to the first light outlet or to the direction of incidence; only the characteristic emission spectrum of the light source is detected through this second opening. When the globe photometer is used to make an incident light measurement, the globe is provided with an additional opening, situated diametrically opposite the first light outlet. The fraction of the light reflected from the test piece into the globe photometer is preferably focussed through this additional opening onto the entrance of a fiber-optics waveguide by means of an optical projection lens. The other end of the waveguide is connected to the entrance slit of a downstream spectrum-resolving, light-dispersing photosensitive photodetector device for detecting the wave-length-dependent intensity spectrum.

In contrast to the type of globe photometer used for reflected light measurements, the illumination source is placed on one side of the test piece, and the optical assembly which collects the transmitted light for a transmission measurement is set up on the opposite side. The light passes through the test piece onto a focusing lens, for example, which is coupled to the entrance end of a fiber-optics waveguide, which carries the light to the entrance slit of a light-dispersing device, preferably a monochromator, e.g., a grating monochromator.

So that the relative spectral energy distributions $\Phi_P$, $\Phi_R$, and $\Phi_S$ on the one hand and the relative spectral energy distributions $\Phi_{ki,i=1,2,3}(\lambda)$ on the other can be measured without interactions in the area of the entrance to the spectrometer, and especially so that no signals are superimposed on any others, individual diaphragms, which can be opened and closed independently of each other, are installed in the two beam paths. The use of fiber-optics waveguides also offers the advantage that the measurement device can be connected flexibly to the light-analyzing and detecting device, which means that the measuring device can be moved and positioned freely over the test piece surface area to be studied. The use of flexible fiber-optics waveguides also has the advantage that several globe photometer measuring devices can be provided, each of which can be set up independently of the others in a different measuring position. The light signals transmitted by these individual measuring stations are sent separately other and in succession to a light-dispersing device for detection and analysis by way o diaphragm multiplier device.

DETAILED DESCRIPTION OF THE PREFERRED EMBODIMENT

Figure 2:
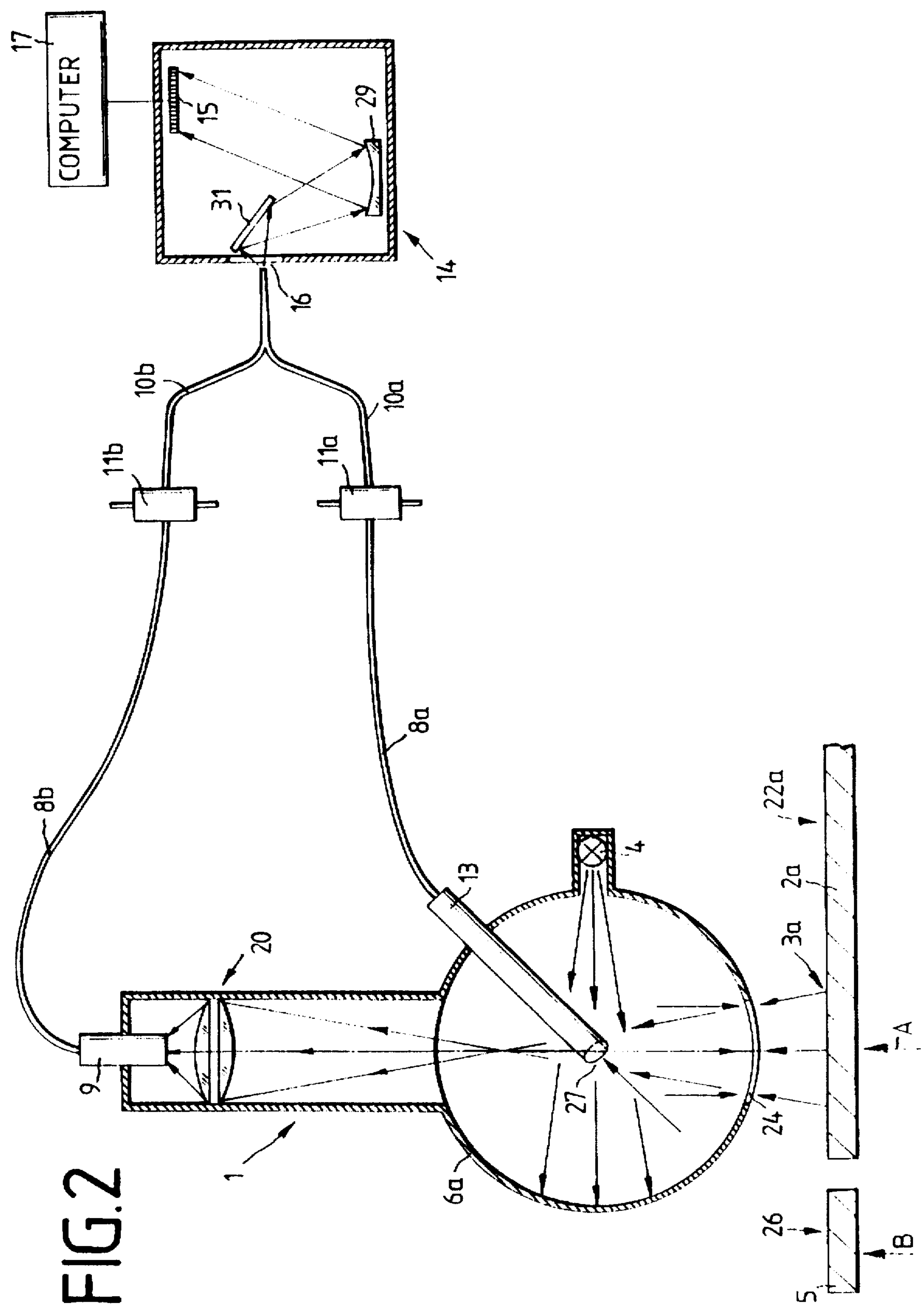
FIG. 2 shows a schematic diagram of a measuring device for implementing the process according to the invention for reflected light measurements.

The measuring device for reflected for incident light measurements is shown in FIG. 2. Surface 22a of a test piece 2a to be investigated is irradiated with the light emerging from an opening 24 in a globe photometer 6a in the form of an Ulbricht sphere. A lamp 4 is positioned in globe photometer 6a to serve as the light source. The light emitted by lamp 4 is scattered diffusely by multiple reflection from the inside walls of globe photometer 6a and ultimately falls essentially at a right angle onto an area 3a of surface 22a to be studied. The light which is reflected either in an orderly or diffuse manner from test piece surface 3a, 22a back into the globe photometer is focused by a set of lenses 20, which is provided inside the body of globe photometer 6a diametrically opposite opening 24, onto a coupling piece 9. At the end of coupling piece 9 facing away from the set of lenses 20, the coupler is connected to flexible fiber-optics waveguides 8b and 10b; between waveguides 8b and 10b there is a closable diaphragm 11b. The light bundle transferred from waveguide 8b to waveguide 10b when the diaphragm is open is fed by waveguide 10b at its exit end to entrance 16 of a spectrally dispersing device, preferably a monochromator 14. By way of a mirror 31, the entering light is directed onto an optical grating 29, preferably a concave reflection grating, and thus split up dispersively in space and projected as an image onto a photosensitive photodetector device 15. Photodetector 15 converts the incident light in correspondence with its wavelength-dependent intensity distribution into electrical signals, which are sent for storage and further processing to a computer 17.

To determine the relative spectral energy distributions $\Phi_{ki,i=1,2,3}(\lambda)$ inside globe photometer 6a, the light used to illuminate layer 3a is diverted from the interior of globe photometer 6a through an outbound coupler 13 and through fiber-optics waveguides 8a and 10a to entrance 16 of light-dispersing device 14. Waveguides 8a, 10a can, like waveguides 8b, 10b, be separated in a leak-tight manner from each other by means of a diaphragm 11a, which can be opened and closed as desired. The light sent via waveguides 8a, 10a to light-dispersing device 14 is spectrally resolved, detected by photodetector 15, and sent as wavelength-dependent electrical signals varying in spectral intensity to computer 17 for storage and further processing. A photosensitive CCD array or a photomultiplier, for example, can serve as photodetector 15.

To record the white reference standard spectrum, a press-molded ceramic body 5 is preferably used, consisting preferably of barium sulfate; in any event, surface 26 of the body must generate essentially a white light reflection spectrum. To position outlet/inlet opening 24 over reference surface 26, globe photometer 6a can be moved in a direction parallel to surfaces 3a, 22a, 26 to be studied by means of a transport device not shown in FIG. 2. To record the spectral functions $\Phi_P$, $\Phi_R$, $\Phi_S$, and $\Phi_{ki,i=1,2,3}(\lambda)$ for determining the diffuse reflectance curve $\beta(\lambda)$, the light sent via waveguides 8a, 10a and 8b, 10b is sent individually and in alternation to light-dispersing device 14 by the use of diaphragms 11a, 11b. To simplify the construction of the device, it is provided that waveguides 10a, 10b form a Y-type waveguide, the common guide strand being positioned in front of entrance slit 16 of light-dispersing device 14.

According to the invention, a halogen lamp is provided as lamp 4, and it is allowed to burn continuously. As an alternative to lamp 4 installed directly in globe photometer 6a, it is also possible to illuminate the interior of globe photometer 6a from the end of a waveguide component, not shown in FIG. 2, which projects through an opening provided in globe photometer 6a and which is essentially at a right angle to outlet opening 24, outbound coupler 13, and the beam path defined by set of lenses 20. The alignment of lamp 4 at a right angle to outlet/inlet opening 24, outbound coupler 13, and optical lens array 20 ensures that the light emerging from globe photometer 6a through outlet 24 and the light emerging through outbound coupler 13 do not differ from each other with respect to their spectral intensity distribution. The light being sent out through inlet opening 27 of coupler 13 can be used to determine the apparatus-related spectral functions $\Phi_{ki,i=1,2,3}(\lambda)$.

Figure 1:
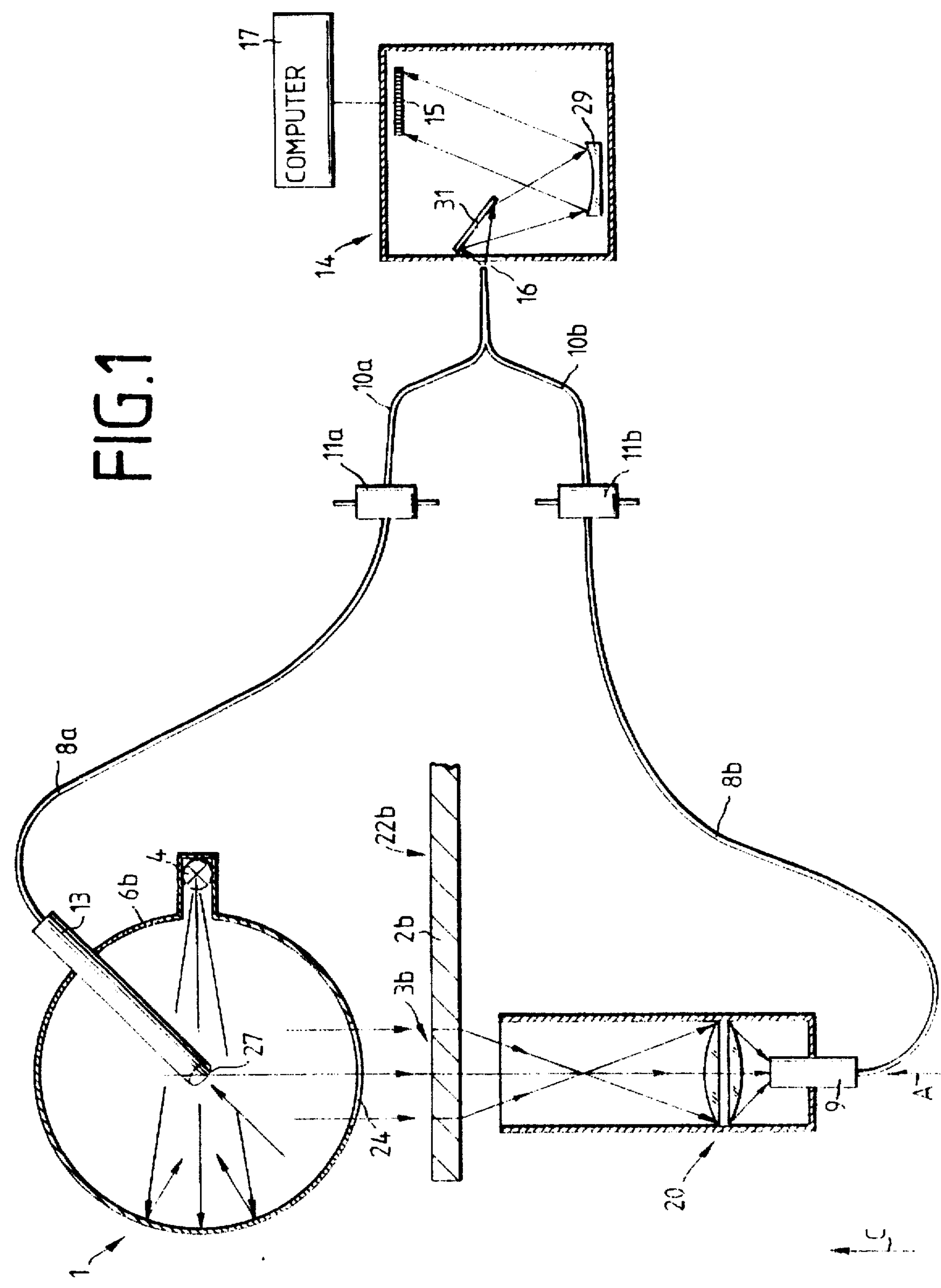
FIG. 1 shows a schematic diagram of a measuring device for implementing the process according to the invention for transmission measurements.

Measuring device 1 shown schematically in FIG. 1 serves to measure the diffuse reflectance curve $\beta(\lambda)$ of a measurement object 2b to be determined in transmission. The light source integrated into globe photometer 6b is on one side of measurement object 2b, and light detection system 20 is on the other. The light emerging from opening 24 in globe photometer 6b falls essentially at a right angle onto measurement surface 22b in the area of layer 3b to be investigated. After the light has passed through measurement object 2b, it is focussed by means of projecting lens 20 on the entrance of an outbound coupler 9. Fiber-optics waveguides 8b, 10b, are separated from each other by a diaphragm 11b, which can close off the path of the beam in a leak-tight manner. These waveguides carry the light which has passed through measurement object 2b to entrance slit 16 of a spectrally dispersive device 14, preferably a grating monochromator. The light is thus split up into its wavelength-dependent intensity components, which, after conversion to electrical signals by means of a photodetector device 15, are sent to a computer 17 for storage and further processing. To record the apparatus-related spectral relative spectral energy distributions $\Phi_{ki,i=1,2,3}(\lambda)$, an outbound coupler 13 is inserted in globe photometer 6b. The light in globe photometer 6b which falls on inlet 27 of the coupler is transferred to a waveguide 8a, which, at the other end, is connected to a closable diaphragm 11a. When diaphragm 11a is open, the light emerges from waveguide 8a and enters a waveguide 10a, next to the exit end of waveguide 8a, and is thus carried to entrance slit 16 of spectrally dispersive device 14. Here it is broken down into its spectrum by a reflection grating 29 and converted into electric signals of varying intensities, which are sent to a computer 17 for storage and further mathematical processing.

Fiber-optics waveguides 10a, 10b take the form here of a so-called "optical brancher", which, in the exemplary embodiment showed in FIGS. 1 and 2, is designed as a Y-type waveguide.

To eliminate the effects of foreign light on the measurement of the apparatus-related spectral functions $\Phi_{ki,i=1,2,3}(\lambda)$, inlet opening 27 is preferably at an angle between opening 24 and reflected light from lamp 4 in globe photometer 6b. This prevents the light which is shining through opening 24 into globe photometer 6b from arriving directly at opening 27 and also has the effect that the light radiated by lamp 4 must be reflected several times inside globe photometer 6b before it can leave through opening 27 in the form of a diffusely scattered light distribution.

What is claimed is:

1. Optical measuring apparatus for determining chromaticity of thin films on a substrate, said apparatus comprising
   measuring apparatus including means for dispersing light into various wavelengths and means for making wavelength-dependent intensity measurements,
   a light source for illuminating a substrate and causing light to be reflected from said substrate,
   first transmission means for transmitting light reflected from said substrate along a first beam path to said measuring apparatus, said first transmission means having therein first diaphragm means for cutting off said first beam path in a leak-tight manner,
   second transmission means for transmitting light emitted from said light source along a second beam path to said measuring apparatus, said second transmission means having therein second diaphragm means for cutting off said second beam path in a leak-tight manner, whereby
   by alternately cutting off said first and second light beams, wavelength dependent intensity measurements for light reflected from said substrate and for light emitted from said light source can be made independently.

2. Apparatus as in claim 1 wherein said light source comprises an Ullbricht sphere having an inside surface, and means for illuminating said inside surface, said first transmission means comprising an opening in said sphere for illuminating said substrate and reflecting light back into said sphere along said first beam path, said second transmission means comprising an inlet opening for receiving light reflected from said inside surface along said second beam path.

3. Optical measuring apparatus for determining chromaticity of thin films on a substrate, said apparatus comprising
   measuring apparatus including means for dispersing light into various wavelengths and means for making wavelength-dependent intensity measurements,
   a light source for illuminating a substrate and causing light to be transmitted through said substrate,
   first transmission means for transmitting light transmitted through said substrate along a first beam path to said measuring apparatus, said first transmission means having therein first diaphragm means for cutting off said first beam path in a leak-tight manner,
   second transmission means for transmitting light emitted from said light source along a second beam path to said measuring apparatus, said second transmission means having therein second diaphragm means for cutting off said second beam path in a leak-tight manner, whereby
   by alternately cutting off said first and second light beams, wavelength dependent intensity measurements for light transmitted through said substrate and for light emitted from said light source can be made independently.

4. Apparatus as in claim 3 wherein said light source comprises an Ullbricht sphere having an inside surface, and means for illuminating said inside surface, said first transmission means comprising an opening in said sphere for illuminating said substrate and transmitting light through said substrate along said first beam path, said second transmission means comprising an opening for receiving light reflected from said inside surface along said second beam path.

5. Process for measuring the optical properties of transparent-reflective and/or reflective objects as a function of the wavelength of the light, preferably for measuring the optical properties of thin layers (3$a$) applied by a vacuum coating process, with a light source (4, 6$a$), a spectrally resolving, light-dispersing device (14), a photodetector device (15), and an electronic evaluation unit (17), which electronically stores and displays the intensity signals of the light spectra detected by the photodetector device (15) as a function of the wavelengths λ of the light, where a first component of the light emitted by light source (4) is diverted to the object surface (3$a$, 22$a$, 26); in that the light reflected as a function of the nature of the surface (3$a$, 22$a$, 26) is diverted to the inlet opening (16) of the light-dispersing device (14) for the measurement of a spectral relative spectral energy distribution $\Phi(\lambda)$; and in that a second component of the light emitted by the light source is diverted directly onto the inlet opening (16) of the light-dispersing device (14) for the determination of a spectral apparatus function $\Phi_{ki,i=1,2,3}(\lambda)$ of the light source (4, 6$a$), the measuring method comprising the following measurement steps:

(a) the spectral relative spectral energy distribution $\Phi_P(\lambda)$ on the object surface (3$a$, 22$a$) is measured;

(b) the spectral apparatus function $\Phi_{ki}(\lambda)$ of the light source (4, 6$a$) is measured;

(c) the spectral relative spectral energy distribution $\Phi_R(\lambda)$ on a reference surface (26) is measured;

(d) the spectral apparatus function $\Phi_{k2}(\lambda)$ of the light source (4, 6$a$) is measured;

(e) the spectral relative spectral energy distribution $\Phi_S(\lambda)$ of the measurement field without the test piece is measured to determine the relative spectral energy distribution $\Phi_S(\lambda)$ of the test piece background;

(f) the spectral apparatus function $\Phi_{k3}(\lambda)$ of the light source (4, 6$a$) is measured;

(g) the wavelength-dependent relative spectral energy distribution ratios $\beta_P(\lambda)$, $\beta_R(\lambda)$, and $\beta_S(\lambda)$ are calculated according to:

$$\beta_P(\lambda)=\frac{\Phi_P(\lambda)}{\Phi_{k1}(\lambda)}, \quad \text{(I)}$$

$$\beta_R(\lambda)=\frac{\Phi_R(\lambda)}{\Phi_{k2}(\lambda)}, \quad \text{(II)}$$

$$\beta_S(\lambda)=\frac{\Phi_S(\lambda)}{\Phi_{k3}(\lambda)}, \quad \text{(III)}$$

and the diffuse reflectance curve $\beta(\lambda)$ according to:

$$\beta(\lambda)=\frac{\beta_P(\lambda)-\beta_S(\lambda)}{\beta_R(\lambda)-\beta_S(\lambda)}, \quad \text{(IV)}$$

and (h) the diffuse reflectance curve $\beta(\lambda)$ is stored electronically so that it can be displayed graphically and used for further calculations of wave-length-related optical characteristics of the object surface (3$a$, 22$a$, 26) from the diffuse reflectance curve $\beta(\lambda)$.

6. Process according to claim 5 wherein the light source is designed as a globe photometer (6$a$) illuminated from the inside and in that a part of the emitted light is diverted through an outlet opening (24) in the globe photometer (6$a$, 6$b$) opposite the measurement surface (33$a$, 22$b$) onto the test piece (2$a$, 2$b$, 26).

7. Process according to claim 5 wherein the light reflected from the measurement surface (3$a$, 22$a$, 26) into the globe photometer (6$a$) is carried by means of projecting lens (20) diametrically opposite the outlet opening (24) to the entrance slit (16) of the light-dispersive device (14), and in that the globe photometer (6$a$) has at least one additional opening (27), through which a part of the light radiation generated inside the globe photometer (6$a$) is diverted onto the entrance slit (16) of the light-dispersing device (14) for the determination of the apparatus-related relative spectral energy distributions $\Phi_{ki,i=1,2,3}(\lambda)$.

8. Process according to claim 5 wherein the light radiation generated in globe photometer (6$a$) is generated by a lamp (4), which shines into the globe photometer (6$a$) and which is essentially at right angles to the outlet openings (24, 27), or by the light-emitting end of a fiber-optics waveguide, which shines into the globe photometer (6$a$), the other end of the guide being illuminated by a lamp.

9. Process according to claim 5 wherein a halogen lamp is used as the lamp (4), which is preferably allowed to burn continuously.

10. Process according to claim 5 wherein the light sent out through opening (27) and the light sent by projecting lenses (20) are carried by fiber-optics waveguides (8$a$, 8$b$; 10$a$, 10$b$) to the entrance slit (16) of the light-dispersing device (14), at least one diaphragm (11$a$, 11$b$) being assigned to each of the individual waveguide routes (8$a$, 10$a$; 8$b$ 10$b$), by means of which one of the beam paths is selected to allow the passage of the light so that the relative spectral energy distributions $\Phi_P(\lambda)$, $\Phi_S(\lambda)$, $\Phi_R(\lambda)$ or $\Phi_{ki,i=1,2,3}(\lambda)$ can be measured.

11. Process according to claim 5 wherein a white reference standard, preferably a press-molded blank of barium sulfate or magnesium oxide or a flat body (26) made of ceramic, is used as the reference surface (26).

12. Process for measuring the optical properties of transparent-reflective and/or transparent objects as a function of the wavelength of the light, preferably for measuring the optical properties of thin layers (3$b$) applied by means of a vacuum coating process, with a light source (4, 6$b$), a spectrally resolving, light-dispersing device (14), a photodetector device (15), and an electronic evaluation unit (17), which electronically stores and displays the intensity signals of the light spectra detected by the photodetector device (15) as a function of the wavelength λ of the light, where a first component of the light emitted by the light source (4, 6$b$) is diverted onto the object surface (3$b$, 22$b$); in that the light transmitted as a function of the nature of the illuminated test piece surface (3$b$, 22$b$) is diverted onto the entrance (16) of the light-dispersing device (14) for measuring a spectral relative spectral energy distribution $\Phi(\lambda)$; and in that a second component of the light emitted by the light source (4, 6$b$) is diverted directly onto the entrance (16) of the light-dispersing device (14) for the determination of the spectral apparatus functions $\Phi_{ki,i=1,2,3}(\lambda)$ of the light source (4, 6$b$), the measuring process comprising the following measurement steps:

(a) the spectral relative spectral energy distribution $\Phi P(\lambda)$ of the light on the test piece surface (3$b$, 22$b$) which is transmitted by the measurement object (2$a$) is measured;

(b) the spectral apparatus function $\Phi_{ki}(\lambda)$ of the light source (4, 6$b$) is measured;

(c) the spectral relative spectral energy distribution in a measurement position (C) without a measurement object is measured to determine a reference relative spectral energy distribution $\Phi_R(\lambda)$, the light emerging from the light source (4, 6b) being sent preferably directly to the projection lens (20);

(d) the spectral apparatus function $\Phi_{k2}(\lambda)$ of the light source (4, 6b) is measured;

(e) the wavelength-dependent relative spectral energy distribution ratios $\beta_P(\lambda)$, $\beta_R(\lambda)$, and $\beta_S(\lambda)$ are calculated according to:

$$\beta_P(\lambda)=\frac{\Phi_P(\lambda)}{\Phi_{k1}(\lambda)}, \quad (I)$$

$$\beta_R(\lambda)=\frac{\Phi_R(\lambda)}{\Phi_{k2}(\lambda)}, \quad (II)$$

and the diffuse reflectance curve $\beta(\lambda)$ according to:

$$\beta(\lambda)=\frac{\beta_P(\lambda)}{\beta_R(\lambda)}. \quad (IV)$$

and (h) the diffuse reflectance curve $\beta(\lambda)$ is stored electronically so that it can be displayed graphically and used for further calculations of wave-length-related optical characteristics of the object surface (3b, 22b) from the diffuse reflectance curve $\beta(\lambda)$.

13. Process according to 12 wherein the light radiation generated in the globe photometer (6b) is generated by means of a lamp (4), which shines into the globe photometer (6b) and which is set up at right angles to the outlet openings (24, 27), or by the light-emitting end of a fiber-optics waveguide, which shines into the globe photometer (6b), the other end of the waveguide being illuminated by a lamp.

14. Process according to claim 12 wherein a halogen lamp is used as the lamp (4), which is preferably allowed to burn continuously.

15. Process according to claim 12 wherein the light sent out from outlet (27) and the light sent by projection lens (20) are carried preferably by means of fiber-optics waveguides (8a, 8b, 10a, 10b) to the entrance slit (16) of the light-dispersing device (14), at least one diaphragm (11a, 11b) being assigned to each of the individual routes of the waveguides (8a, 10a), by means of which one of the beam paths can be selected to allow the transmission of the light for the selective measurement of the relative spectral energy distributions $\Phi_P(\lambda)$, $\Phi_R(\lambda)$, and $\Phi_{ki}(\lambda)$.

16. Process according to claim 12 wherein the relative spectral energy distributions $\Phi_P(\lambda)$, $\Phi_S(\lambda)$, $\Phi_R(\lambda)$, and $\Phi_{ki,\, i=1,2,3}(\lambda)$ are each measured several times and added, and in that from the additive function values thus obtained, average function values are calculated, from which the relative spectral energy distribution ratios $\beta_P(\lambda)$, $\beta_R(\lambda)$, and $\beta_S(\lambda)$ and the diffuse reflectance curve $\beta(\lambda)$ are calculated.

17. Process according to claim 12 wherein the process is used in particular to monitor and/or automatically control a vacuum-assisted thin-film production process.

* * * * *